United States Patent
Campos

(10) Patent No.: US 7,035,691 B2
(45) Date of Patent: Apr. 25, 2006

(54) RESONANT MUSCLE STIMULATOR

(75) Inventor: James M. Campos, Hayward, CA (US)

(73) Assignee: Therapeutic Innovations, Inc., Crescent Springs, KY (US)

( * ) Notice: Subject to any disclaimer, the term of this patent is extended or adjusted under 35 U.S.C. 154(b) by 419 days.

(21) Appl. No.: 10/047,745

(22) Filed: Jan. 15, 2002

(65) Prior Publication Data

US 2003/0135245 A1 Jul. 17, 2003

(51) Int. Cl.
*A61N 1/36* (2006.01)

(52) U.S. Cl. .................................. 607/48; 607/72

(58) Field of Classification Search .................. 607/40, 607/48, 49, 68, 70, 72, 73, 74
See application file for complete search history.

(56) References Cited

U.S. PATENT DOCUMENTS

| | | | |
|---|---|---|---|
| 267,025 A | 11/1882 | See | |
| 310,733 A | 1/1885 | Shaw | |
| 311,381 A | 1/1885 | Shaw | |
| 341,593 A | 5/1886 | McGinnis | |
| 451,936 A | 5/1891 | Jolly | |
| 920,837 A | 5/1909 | Moulin | |
| 1,583,261 A | 5/1926 | Sence | |
| 2,350,797 A | 6/1944 | Morland et al. | 250/36 |
| 3,424,165 A | 1/1969 | Moss | 128/405 |
| 3,911,930 A * | 10/1975 | Hagfors et al. | 607/46 |
| 3,946,745 A | 3/1976 | Hsiang-Lai et al. | 128/421 |
| 4,121,594 A | 10/1978 | Miller et al. | 128/422 |
| 4,177,819 A | 12/1979 | Kofsky et al. | 128/422 |
| 4,233,986 A | 11/1980 | Tannenbaum | 128/421 |
| 4,279,256 A | 7/1981 | Bucalo | 128/419 |
| 4,338,945 A | 7/1982 | Kosugi et al. | 128/421 |
| 4,372,319 A | 2/1983 | Ichinomiya et al. | 128/421 |
| 4,434,798 A | 3/1984 | Trnkoczy et al. | 128/421 |
| 4,471,784 A | 9/1984 | Kympl | 128/422 |
| 4,480,830 A * | 11/1984 | Petrofsky et al. | 482/93 |
| 4,503,863 A | 3/1985 | Katims | 128/741 |
| 4,510,936 A | 4/1985 | Fourcin et al. | 128/419 |
| 4,520,825 A | 6/1985 | Thompson et al. | 128/422 |
| 4,541,432 A | 9/1985 | Molina-Negro et al. | 128/421 |
| 4,582,063 A | 4/1986 | Mickiewicz et al. | 128/421 |
| 4,595,010 A | 6/1986 | Radke | 128/421 |
| 4,640,286 A | 2/1987 | Thomson | 128/421 |
| 4,688,574 A | 8/1987 | Dufresne et al. | 128/421 |
| 4,690,145 A | 9/1987 | King-Smith et al. | 128/421 |
| 4,712,558 A | 12/1987 | Kidd et al. | 128/421 |
| 4,763,656 A | 8/1988 | Nauman | 128/421 |
| 4,769,881 A | 9/1988 | Pedigo et al. | 128/419 |
| 4,793,353 A | 12/1988 | Borkan | 128/421 |
| 4,805,621 A | 2/1989 | Heinze et al. | 128/419 |

(Continued)

OTHER PUBLICATIONS

EMPI, *Instruction Manual for the Empi® EPIX XL™ TENS Device*, Instruction Manual, 20 pgs., 1988.

(Continued)

*Primary Examiner*—Kennedy Schaetzle
(74) *Attorney, Agent, or Firm*—Wood, Herron & Evans, L.L.P.

(57) ABSTRACT

A method and apparatus generate resonant sequences having pulses optimally spaced and configured to realize uniform contractions in a musculature. Namely, each subsequent pulse maintains tension within sarcomeres of the musculature as the resonant sequence propagates inwardly to progressively stimulate the entirety of the musculature. Variation in the width, spacing, polarity and/or amplitude of the pulses comprising the resonant sequence further overcomes accommodation and nutritional depletion while minimizing discomfort.

53 Claims, 6 Drawing Sheets

U.S. PATENT DOCUMENTS

| | | | |
|---|---|---|---|
| 4,821,723 A | 4/1989 | Baker, Jr. et al. | 128/419 |
| 4,838,272 A * | 6/1989 | Lieber | 607/48 |
| 4,919,139 A | 4/1990 | Brodard | 128/421 |
| 4,922,908 A | 5/1990 | Morawetz et al. | 128/422 |
| 4,926,865 A | 5/1990 | Oman | 128/421 |
| 4,947,836 A | 8/1990 | Laenger et al. | 128/419 |
| 4,947,844 A | 8/1990 | McDermott | 128/421 |
| 4,949,721 A | 8/1990 | Toriu et al. | 128/421 |
| 4,960,124 A | 10/1990 | Masaki | 128/421 |
| 5,018,524 A | 5/1991 | Gu et al. | 128/421 |
| 5,031,618 A | 7/1991 | Mullett | 128/421 |
| 5,033,468 A | 7/1991 | Takeuchi et al. | 128/421 |
| 5,036,850 A | 8/1991 | Owens | 128/421 |
| 5,067,495 A | 11/1991 | Brehm | 128/421 |
| 5,069,211 A | 12/1991 | Bartelt et al. | 128/421 |
| 5,081,989 A | 1/1992 | Graupe et al. | 128/419 |
| 5,097,833 A | 3/1992 | Campos | 128/421 |
| 5,133,354 A * | 7/1992 | Kallok | 607/48 |
| 5,183,041 A | 2/1993 | Toriu et al. | 128/421 |
| 5,193,539 A * | 3/1993 | Schulman et al. | 607/61 |
| 5,211,173 A * | 5/1993 | Kallok et al. | 607/42 |
| 5,251,637 A | 10/1993 | Shalvi | 128/735 |
| 5,281,219 A | 1/1994 | Kallok | 607/42 |
| 5,291,883 A | 3/1994 | Kreutner | 128/421 |
| 5,350,414 A | 9/1994 | Kolen | 607/62 |
| 5,350,415 A | 9/1994 | Cywinski | 607/68 |
| 5,385,530 A | 1/1995 | Wu | 601/21 |
| 5,411,525 A | 5/1995 | Swanson et al. | 607/5 |
| 5,433,737 A | 7/1995 | Aimone | 607/72 |
| 5,456,709 A | 10/1995 | Hamedi | 607/138 |
| 5,476,504 A | 12/1995 | Paolizzi | 607/150 |
| 5,507,781 A | 4/1996 | Kroll et al. | 607/7 |
| 5,514,167 A | 5/1996 | Smith et al. | 607/75 |
| 5,540,721 A | 7/1996 | Kroll | 607/5 |
| 5,575,809 A | 11/1996 | Sasaki | 607/62 |
| 5,593,427 A | 1/1997 | Gliner et al. | 607/7 |
| 5,601,608 A | 2/1997 | Mouchawar | 607/5 |
| 5,607,461 A | 3/1997 | Lathrop | 607/75 |
| 5,609,618 A | 3/1997 | Archer | 607/74 |
| 5,626,628 A | 5/1997 | Ganansia | 607/47 |
| 5,643,329 A * | 7/1997 | Solomonow et al. | 607/43 |
| 5,643,331 A | 7/1997 | Katz | 607/48 |
| 5,702,423 A | 12/1997 | Hujimaki | 607/2 |
| 5,702,428 A | 12/1997 | Tippey et al. | 607/41 |
| 5,735,879 A | 4/1998 | Gliner et al. | 607/7 |
| 5,797,964 A | 8/1998 | Carlson et al. | 607/2 |
| 5,800,503 A | 9/1998 | Edmark et al. | 607/145 |
| 5,817,030 A | 10/1998 | Tarjan et al. | 600/546 |
| 5,817,141 A | 10/1998 | Iimori | 607/76 |
| 5,817,142 A | 10/1998 | Corder | 607/76 |
| 5,868,653 A | 2/1999 | Klasen | 482/110 |
| RE36,260 E | 7/1999 | Smith et al. | 607/75 |
| 2002/0010498 A1 * | 1/2002 | Rigaux et al. | 607/62 |

OTHER PUBLICATIONS

Rich-Mar Corporation, *Rich-Mar H.V. 20,* Brochure, 4 pgs., 1987.

Mettler Electronics Corp., *Muscle Stimulator User Manual,* Jun. 1986, 6 pgs.

* cited by examiner

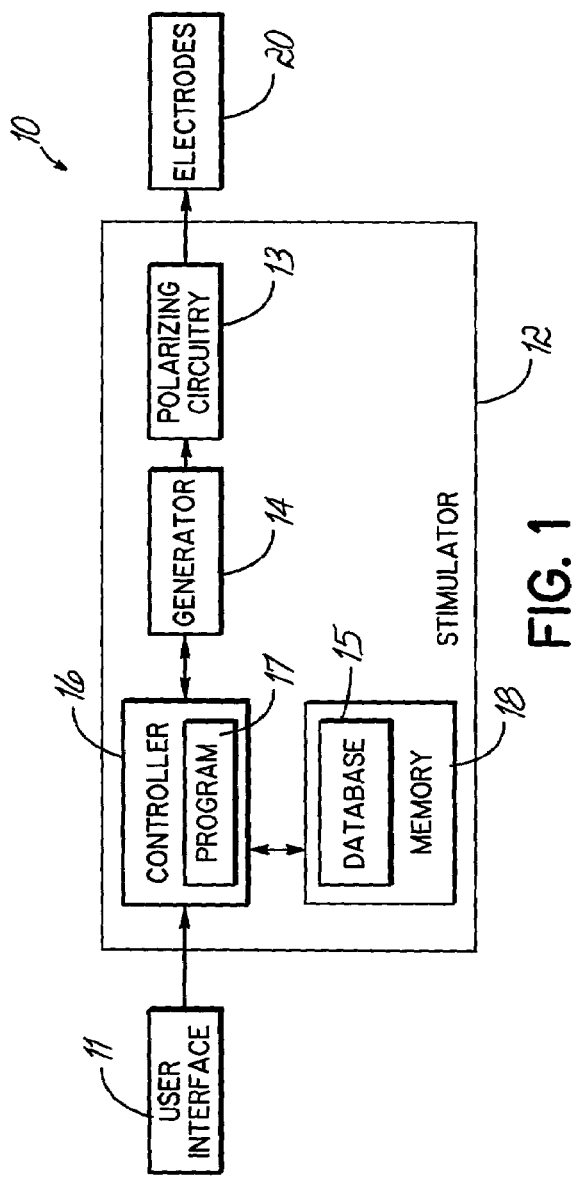
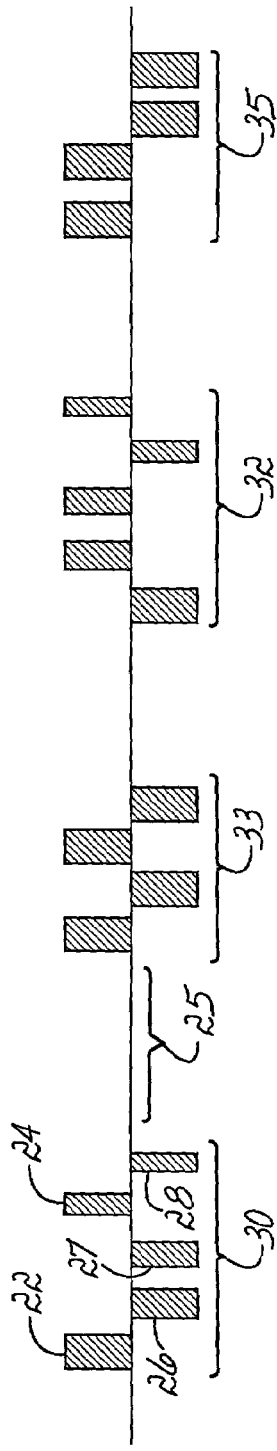
FIG. 1
FIG. 2

RESONANT MUSCLE STIMULATOR

FIELD OF THE INVENTION

The present invention relates generally to the field of electronic muscle stimulation, and more particularly to transcutaneous muscle development.

BACKGROUND OF THE INVENTION

The ability to stimulate or exercise muscle tissue is critical to the development and rehabilitation of muscle. In nature, alterations in ion channels cause the brain to generate electronic impulses or synapses. An impulse propagates along an axon to its termination on its way to initiating a muscle contraction. As such, characteristics of the impulse complement the active processes of the nervous system. Mechanically generated attempts to stimulate muscles often strive to emulate natural impulses, working within the confines of axon receptors. Therapists and athletes use machines that produce variations of such signals to develop muscle tissue by inducing a series of contractile twitches that aggregate to form a contraction. Benefits of such stimulation include the promotion of blood flow and the localized development of muscle tissue.

Conventionally, such signals embody a series of discontinuous pulses. Despite charges being measurable in millivolts, each pulse communicates at least a minimum threshold potential to a muscle. A threshold potential corresponds to a voltage level, or charge, as measured at a motor nerve, where the membrane of an axon experiences depolarization. Also called a firing level, it coincides with the moment of a twitch, where the potential in the axon releases its energy into a calcium/adenosine triphosphate (ATP) union at one or more toggling bridges in the sarcomere until the axon arrives at zero potential.

In this manner, the threshold potential presented via each pulse initiates a full-fledged twitching reaction. That is, sarcomere tissue of a muscle creates one twitch worth of contractile force in response to an application of a generated threshold potential. Successive bridging of adjacent sarcomere tissue comprises a contraction. Of note, a toggling reaction will not occur if the stimulus is sub-threshold in magnitude, i.e., it fails to convey the requisite threshold potential. The contractile reaction at each bridge in the sarcomere is therefore all-or-none. In this manner, conventional techniques repeat pulses of identical potential and duration to produce consecutive twitches that add up to a contraction. In this manner, each pulse of a signal will theoretically stimulate a next twitch.

In nature, sarcomere bridges toggle simultaneously across the length of each muscle as individual twitches aggregate to form a single contraction. In this manner, the twitches are said to toggle uniformly across a muscle. Such uniformity evades electrical attempts to stimulate muscle. In contrast, conventional applications use single short pulses that may succeed in toggling a high concentration of sarcomere bridges near the electrodes, but ultimately fail to stimulate more distant bridges. That is, while a high frequency application may initially toggle more bridges, the shorter spacing of the pulses is too small to allow time for depolarization and nutritional replenishment, ultimately frustrating continuing contraction.

As such, any contractile reaction initiated by the pulse is ended within a fraction of a second. Conversely, if the pulse rate is made slow enough to allow for depolarization and nutritional replenishment, accommodation drops in proportion to the drop in frequency, thus the deeper penetration is made possible. However, penetration comes at the expense of pain from the yanking and dropping effect produced by the toggling, de-toggling, re-toggling of more and more bridges in more sarcomeres with the increase in time between pulses as the frequency drops.

Other prior art techniques attempt to affect larger portions of the muscle by extending pulse length. However, such attempts still fail to achieve a uniform contraction. Namely, sarcomere bridges of the portion of the muscle nearest to the electrodes will release due to polarization and nutritional problems prior to an adjacent portion of the muscle toggling. The duration of the pulse causes the bridges in sarcomeres closer to the center of the muscle to toggle, but only at the cost of painfully yanking the spent and relaxing sarcomeres nearest the electrodes into a stretched condition as the process travels in a wave or ripple effect outward from the electrodes, but inward toward each other.

By the time the bridges in the middle sarcomeres begin to toggle, the mass of the muscle has developed a crushing velocity to add to the twitch. Those sarcomeres of the muscle nearest the electrodes have already been spent. Despite the relatively weaker twitch of the center sarcomeres, the hyper-compression, as the sum of the above, nonetheless, tugs on adjacent sarcomeres. Over time, repeated applications will increasingly stress and deplete energy supplies of muscle tissues. Repeated applications further produce relatively little beneficial effect, because the muscles are being stretched out of shape, traumatized almost as much as they are being treated. Additionally, high currents associated with long pulses stings the skin of the user. Thus, stimulation of sarcomeres distally positioned from the electrodes has not been possible without incurring preclusive pain and potential damage.

Known techniques used to address such factors include incorporating periods of recovery in between pulses. Sufficient lengths of such periods may allow the muscle to partially prepare for another contractile twitch. Muscle may use this short period between pulses to replenish a portion of expended ATP and calcium ions before the contraction process continues, re-initiated by a subsequent pulse. Each rest time between pulses also allows the body an opportunity to partially reset electrical polarities skewed by its preceding pulse by dissipating capacitance retained in the skin.

Despite these provisions, known pulse applications still suffer diminished returns with successive pulses due to nutritional depletion and motor-nerve boredom. Unless the pulse rate is so slow that it causes a painful, jerking sensation, there is inadequate time between pulses to allow for complete replenishment and electrical recovery. Consequently, pulses of repeated strength and duration incrementally drain overall muscle resources. As the muscles strength and supply wane, so does the muscle's ability to contract. As such, a subsequent pulse, identical in polarity, amplitude, shape and timing produces shallow contractions that result in less penetration than the preceding pulse. Less penetration translates into less muscle development, as weaker contractions fail to increase blood flow to required muscle tissue levels as needed for muscle development.

Still other obstacles hinder the effectiveness of conventional pulse signal applications. Namely, accommodation may prevent repeated pulses from penetrating deeply into the muscle, mitigating the potential benefit of successive pulses. Muscle accommodation regards the ability of the body to adapt to constant and repeated stimuli. Such stimuli includes the successive pulses of conventional muscle stimulators. As such, a muscle adapts to subsequent pulses in such a manner as it fails to achieve the same level of potential in response to a repeated pulse. Two major factors contributing to accommodation relate to electrical polarity and nutritional supply as discussed herein.

To compensate for the detrimental effects of accommodation, some applications attempt to increase the voltage of subsequent pulses to maintain comparable levels of stimulation. Other applications attempt to combat accommodation by varying pulse shape, width, height and frequency. Although such techniques can realize somewhat greater contractile reactions with less voltage, a targeted muscle still twitches in response to each pulse to a lesser degree than to the previous pulse. Further, while marginally effective in temporarily achieving deeper penetration, such attempts still result in preclusive pain that frustrates further treatment. In part, this pain stems from inability of known application and pulse variations to affect motor nerves (associated with muscle development) to the same degree as sensory nerves (associated with pain). In this manner, conventional pulse designers are limited in the range of voltage they can apply and the depth of contractile reactions they can achieve.

Significantly, conventional techniques further fail to uniformly address different types of muscle implicated in a treatment/development session. An inability of prior art pulse applications to simultaneously and consistently stimulate both slow and fast twitch muscle types often results in disproportionate muscle development. Such undesirable development detrimentally impacts balance, mobility and other motor considerations. The absence of uniformity is, in part, a product of how a single pulse induces different reactions in dissimilar muscle types of a user. For instance, as a signal propagates through a patient or athlete, fast and slow twitch muscles respond differently to conventional pulses. This limitation is a product of the different sensitivities and reaction rates of slow and fast twitch muscles.

Fast twitch muscle is developed in response to frequent, quick use. Fast twitch muscle is common in muscle groups that control fine motor functions, such as the wrist and hand. Consequently, fast twitch muscles process electrical stimuli relatively quickly. Of note, such muscles are prone to tire quickly and are vulnerable to overstimulation, causing tetany, a painful tightening of muscles. In contrast, slow twitch muscles react more slowly to stimuli than do fast twitch muscles, and they tire less easily. Slow twitch muscles are developed where smooth, methodical muscle contractions are common. For instance, regular motions and support realized by muscles of the back will typically develop associated muscles as slow twitch.

The disparate reactive characteristics of slow and fast twitch muscles preclude known transcutaneous signals from uniformly addressing both muscle types. Namely, no conventional pulse train can simultaneously sustain even distribution of contractile twitching reactions throughout both fast and slow twitch muscles. More particularly, a conventional train of pulses having a frequency synchronized with the response time of a fast twitch muscle is too quick for a slow twitch muscle to react to its fullest extent for the voltage applied.

Such an application, to a great degree, fails to stimulate slow twitch muscles and almost exclusively activates fast twitch muscles because the signal fails to propagate profound contractile twitches within the sarcomere of the slow twitch muscle. That is, the signal neglects the slow twitch muscle in favor of the fast twitch when both are inline with a signal, resulting in disproportionate development. Of note, high frequency pulses may still cause overstimulation in the fast twitch muscle. Such over-stimulation causes fast twitch muscles to painfully tighten, ending a therapeutic session before any gain can be realized in the slow twitch muscle.

Conversely, slowing the frequency of pulses so as to target slow twitch muscles can produce dissatisfactory results in fast twitch muscles. Thus, any gains realized in the slow twitch muscle group may be tempered by ineffectual and painful reactions in proximate fast twitch muscles. For instance, slow pulse rates may promote a painful, jerking reaction in fast twitch muscles. As a result, the rate of consecutive pulses may be too infrequent or painfully preclusive to substantially exercise or tax fast twitch muscles relative to the slow twitch muscle. In this manner, fast twitch muscles can act as a barrier to treatment of slow twitch muscles in that the high sensitivity and low pain threshold of the fast twitch muscles precludes more extensive propagation of twitches throughout slower twitch muscles. As such, exercising slow twitch muscles remains a challenge to conventional stimulators.

Consequently, what is needed is a single signal capable of uniformly exercising muscle tissue, while accounting for nutritional, comfort and accommodation considerations.

SUMMARY OF THE INVENTION

The invention addresses these and other problems associated with the prior art by providing in one aspect an apparatus, method, and program product configured to stimulate a musculature. More particularly, embodiments consistent with the invention may apply a resonant sequence of pulses across the musculature. The resonant sequences may progress inwardly toward the center of the musculature via two electrodes positioned near its ends to uniformly initiate a contraction within the musculature.

Each resonant sequence may include at least three pulses. The pulses are spaced relative to one another such that each pulse subsequent to a previous pulse in the sequence is effective to progressively stimulate and create tension in the muscle inwardly from the electrodes and toward the center of the musculature while holding the previously toggled bridges in position. Significantly, tension created in at least a portion of the musculature by each preceding pulse in the resonant sequence is maintained.

Optimized frequencies of the resonant sequences enable the muscle to distinctly register a succession of pulse characteristics within the span of a single contraction. More particularly, the width, spacing, polarity, amplitude and/or shape of pulses comprising a sequence may be varied to combat accommodation and minimize discomfort. Such variation may circumvent the natural tendency of the musculature to adjust to and otherwise accommodate the signal, ultimately translating into deeper muscle penetration and decreased discomfort. Provisions such as shortening the length of successive pulses and the use of faradic waveform characteristics can further enable deeper penetration with relatively smaller quantities and durations of applied voltage.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 illustrates a block diagram of an apparatus suited for generating a signal in accordance with the principles of the present invention;

FIG. 2 shows exemplary signals that may be generated by the apparatus of FIG. 1;

DETAILED DESCRIPTION OF SPECIFIC EMBODIMENTS

Figure 3:
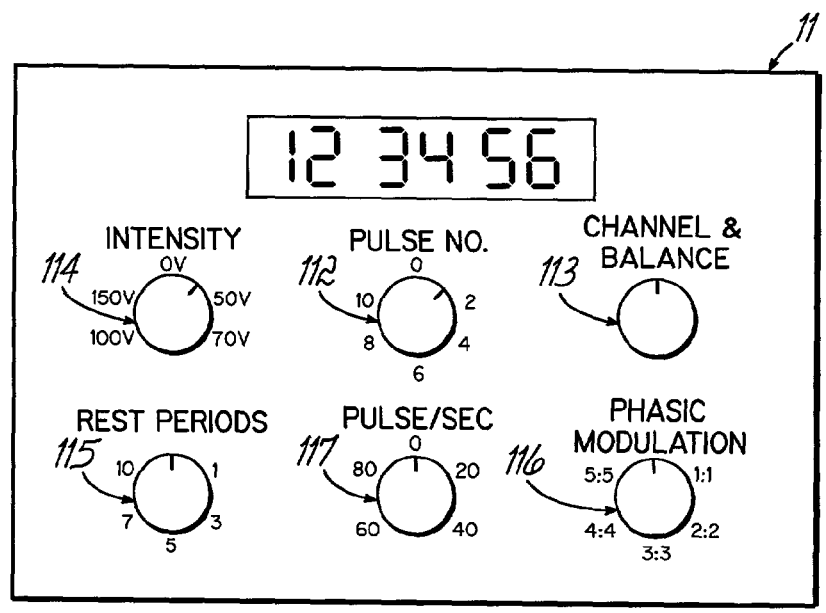
FIG. 3 illustrates a first user interface suited for implementation within the apparatus of FIG. 1.

An apparatus 10 as shown in FIG. 1 and consistent with the principles of the present invention applies resonant sequences of pulses to the skin of a user in order to induce uniform contractile reactions throughout targeted muscle groups. More specifically, the apparatus 10 of FIG. 1 applies the resonant sequence of pulses across a targeted musculature. For purposes of the present invention, a musculature may comprise a single muscle, as well as some muscle combination or chain. The resonant sequences progress inwardly from the opposite ends of the musculature. The resonant sequences each preferably include at least three pulses that are optimally spaced in order to progressively hold and stimulate the bridges of the sarcomeres of the musculature as they travel toward its center. As such, the resonant sequences create tension in the musculature inwardly from the electrodes and toward the center of the musculature. Significantly, the pulses of the sequences are spaced such that their continuous application maintains the tension created in at least a large portion of the musculature by each preceding pulse of the resonant sequence.

In this manner, the musculature is uniformly developed, accounting for patient and athlete balance concerns, and mitigating pain associated with sarcomere stretching, as well as dermal sting associated with excessive current. The uniform development of the apparatus 10 is facilitated by the ability of the resonant sequences to stimulate slow twitch fibers in a fashion that preserves sarcomere bridges throughout the musculature. Because the preservation of the toggled bridges correlates closely to processes associated with a natural contraction, a user is spared pain associated with conventional stimulator applications. Furthermore, the preservation of tension within the musculature reduces the length and amplitude of applied pulses that must be applied to reconstruct a comparable contraction as compared to disjointed pulses of known techniques. As such, the absence of a single, large voltage pulse translates into less discomfort and greater aggregate muscle twitches for the user.

Furthermore, optimized frequencies of resonant sequences enable the musculature to distinctly register a succession of pulse characteristics within the span of a single contraction. More particularly, the apparatus 10 may vary the width, spacing, polarity, amplitude and/or shape of pulses comprising a sequence to combat accommodation and minimize discomfort. Such variation hinders the natural tendency of the musculature to adjust to and otherwise accommodate the signal, ultimately translating into deeper muscle penetration and decreased discomfort.

Generally, FIG. 1 illustrates a user interface 11 coupled to a stimulator 12 and an associated signal generator 14. A controller 16, or suitable microprocessor, may receive input generated from the interface 11. The stimulator 12 may use the input to configure resonant sequences operable to uniformly stimulate targeted muscle groups. To this end, the stimulator 12 may correlate the user input with signal profiles stored in a database 15 resident in a memory 18. As discussed below, each profile may embody signal characteristics optimized to uniformly stimulate muscle tissue with less pain and loss due to accommodation, from polarization and/or nutritional depletion.

As such, the controller 16 may process information extracted from the database 15 for the purpose of sending a command to the signal generator 14. In response to the command, the generator 14 may create a signal that is conveyed to a user via at least two electrodes 20. Of note, a transmission medium suited to convey the signals may comprise multiple cables or circuits, depending on how many channels are conveyed by the generator to the electrodes 20. Furthermore, as discussed below, an embodiment may incorporate circuitry 13 adapted to manipulate the polarity of the signal as discussed below in greater detail.

In response to a command from the stimulator 12 conveying the above-specified parameters, the generator 14 and/or amplifier may create and transmit a signal to the user via the electrodes 20. Of note, the parameters of the generated signal will correspond to those indicated by user input. As shown in FIG. 1 and discussed below in detail, the generator 14 preferably produces additional, complimentary signals for application to additional electrodes 20.

The electrodes 20 of FIG. 1 may contact the skin of a user proximate to a musculature to be exercised or treated. At least two electrodes may be positioned near opposite ends of the musculature. As such, applied signals propagate inwardly from the ends of the musculature towards its center. Of note, the apparatus 10 also permits relatively distant muscle groups to be exercised as the generated signal propagates throughout the body from the electrodes 20. Accordingly, the signal transmitted via the electrodes penetrates and stimulates the various tissues of surrounding muscles according to the generated signal. FIG. 2 illustrates an exemplary signal that may be generated within the environment of FIG. 1.

The signal may convey a series of resonant sequences as shown in FIG. 2. As discussed below in detail, suitable strings of sequences may be distinct and/or mirror/complement each other as prescribed by a given application. Furthermore, the number, width, amplitude, frequency and shape of each pulse of a resonant sequence, or of a resonant sequence, itself, may be selectively modified to achieve a desired effect. Each sequence will preferably include at least three pulses. The frequency of the resonant sequences communicated via the electrode may range generally from about 1 to about 4 kHz. Although the number of pulses may be separately adjustable, such a configuration preferably allows for about 1 to about 100 pulses per second. A single resonant sequence may last for about 6–90 milliseconds. Of note, comparable, conventional pulse frequencies and widths would quickly exhaust the nutrition and skew the electrical balance of a muscle, thus promoting accommodation. As such, the muscle would become unresponsive after only a few pulses, and the patient would likely experience a dermal stinging sensation.

The exemplary signal of FIG. 2 accounts for such conventional obstacles, in part, by interjecting downtime 25 on the order of about 5 to about 500 milliseconds between resonant sequences 30, 32, 33, 35. Such preprogrammed periods 25 of rest enable muscle tissue to replenish energy expended during the prior twitch or contractile advance. As discussed below in detail, the stimulator 12 of FIG. 1 may vary the width, frequency, polarity and/or amplitude of each sequence 30, 32, 33, 35 shown in FIG. 2 as needed to facilitate penetration. Further, the resonant sequences 30, 32, 33, 35 may be evenly or irregularly spaced from one another to combat accommodation and promote deeper contractions.

Individual pulses embedded within each resonant sequence 30, 32, 33, 35 of FIG. 2 further contribute to the stimulation and recovery of different layers of musculature. Configurable characteristics of the pulses provide a mechanism for combating nerve boredom, and nutritional starvation as sources of accommodation while still achieving a threshold potential with less charge and associated pain over a larger number and spread of sarcomeres. As discussed above, threshold potential refers to a minimum charge required to initiate a twitch, that is to say, a toggling of one or more bridges in the affected sarcomere leading up to a contractile reaction. Significantly, each pulse of a resonant sequence may preserve and reinforce sarcomere bridges as the pulse propagates towards the center of a musculature. Such preservation of tension can translate into more natural, deep and uniform contractions as explained below.

Figure 11A:
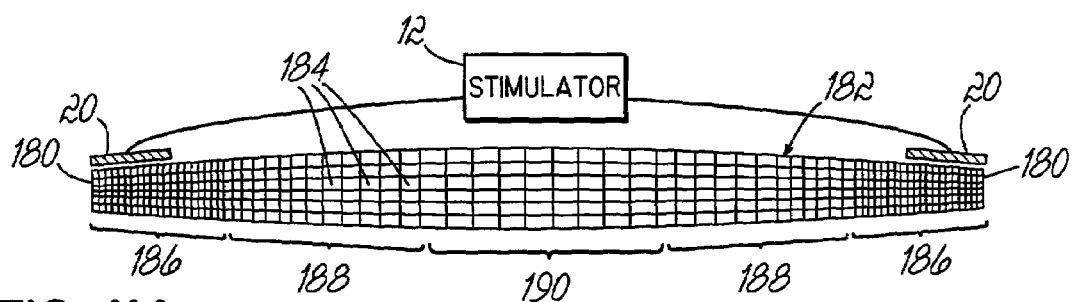
FIGS. 11A–C illustrate a muscle contraction sequence in accordance with the present invention.
Figure 11B:
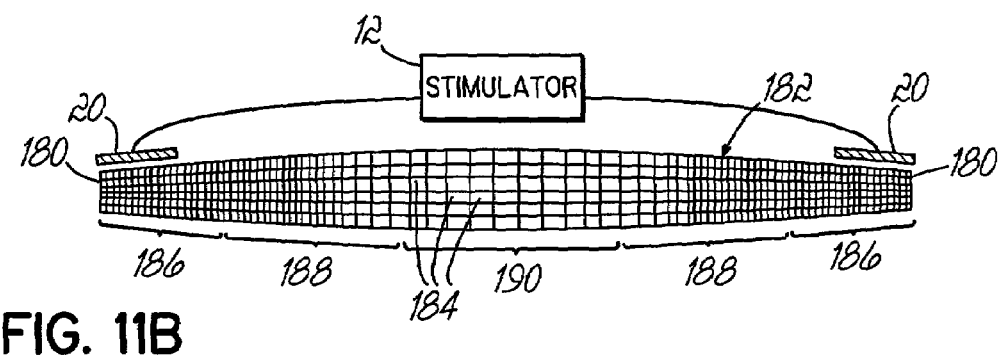
Figure 11C:
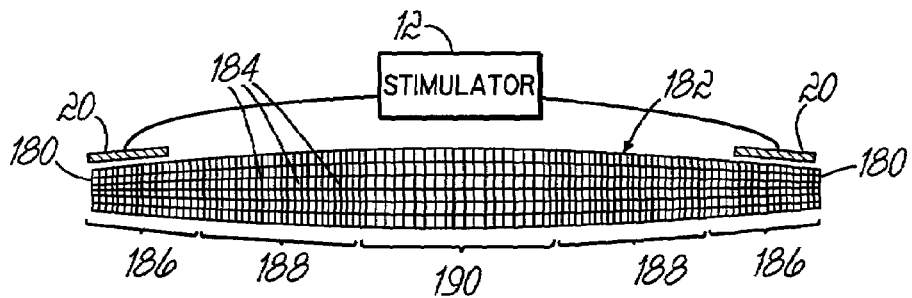

FIGS. 11A–C illustrate an exemplary sequence of such a contraction that is consistent with the principles of the present invention. That is, the sequence shows the propagation of resonant sequences traveling inwardly from poles 180 of a muscle 182. For purposes of FIGS. 11A–C, the resonant sequences arrive from a stimulator 12 via electrodes 20 positioned proximate the poles 180. As such, bridges in sarcomeres 184 closest to the poles 180 of the muscle 182 flex, or toggle, in response to a first pulse of a resonant sequence as illustrated in FIG. 11A. Thus, tension is initiated in extreme portions 186 of the muscle 182 near the poles 180 as the pulse travels inwardly. Assuming that all pulses have the same rise time, that is to say, the same slewing rate, any pulse will start with the same reaction as shown in 11A and 12A. The longer it remains, the more of the cycle depicted in 12A–C is completed until it can respond no longer, untoggles and becomes unresponsive.

Figure 12A:
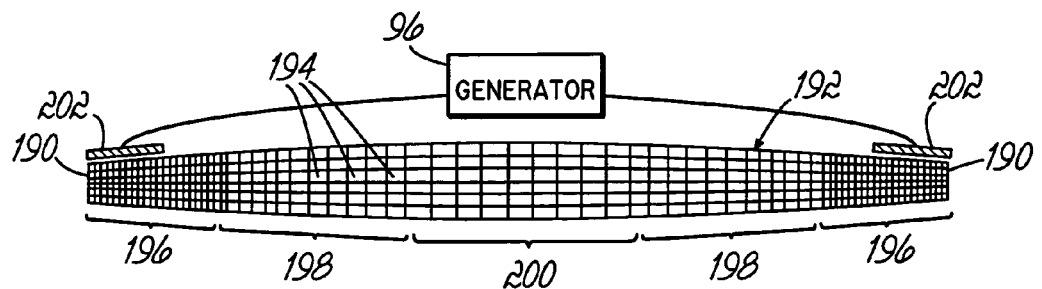
FIGS. 12A–C show a muscle contraction sequence produced by prior art methods and equipment.

To further illustrate significant advantages realized by an embodiment of the invention, the resonant sequence-induced muscle contraction of FIGS. 11A–C is concurrently contrasted against a reaction caused by a single pulse that is long enough to affect a whole muscle or musculature. As shown in FIG. 12A, the reaction initiated by the pulse is nearly identical to the muscle activity of FIG. 11A as the conventional pulse toggles sarcomeres 194 near the electrodes 202. However, superior contractile response and other advantages achieved by the stimulator 92 of FIGS. 11A–C become more apparent as respective resonant sequences travel inwardly from the electrodes 20.

Figure 12B:
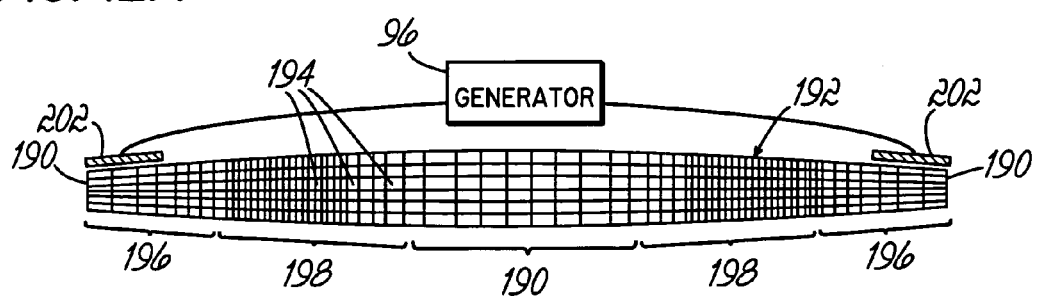

Lead pulses of resonant sequences of FIG. 11B propagate toward each other from the electrodes 20. The sequences initiate toggling of sarcomeres 184 resident in intermediate portions 188 of the muscle 182. Of note, electrical variation in the polarity of the arriving pulses heighten the twitching reaction of the intermediate portions 188 as compared to prior art applications, where accommodation may mitigate contractile response as shown in FIG. 12B. Significantly, the arrival of a second pulse of the resonant sequences of FIG. 11B at the poles 180 has the affect of sustaining bridges initiated by the first pulse within the extreme portions 186.

That is, the second pulse may be spaced from the first by a distance optimized such that the second pulse reinforces and maintains toggling in the extreme portions 186 as the second pulse creates similar tension in the intermediate portions 188. More particularly, the pulses may be spaced at around 3,500–7,000 microseconds. As it may take 10,000 microseconds for sarcomere 184 bridges to toggle off, the prior arrival of the second pulse preempts such bridge disconnection. Of note, variation in pulse characteristics discussed herein facilitate such response by mitigating dampening affects associated with accommodation, as well as electrical and nutritional depletion.

In contrast to the sustained toggling of the extreme portions 186 as discussed above in the text accompanying FIG. 11B, comparable areas 186 of the muscle 190 of FIG. 12B return to a relaxed position over the same period. The prior art application of FIG. 12B may succeed in toggling intermediate portions 198 of the muscle 190, but such bridging is accompanied by an absence of tension in the extreme areas 196. Thus, the inability of the conventional pulses to maintain toggling near the electrodes 202 results in tension traveling arrhythmically across the muscle 190 of FIG. 12B, defeating a uniform contraction.

Figure 12C:
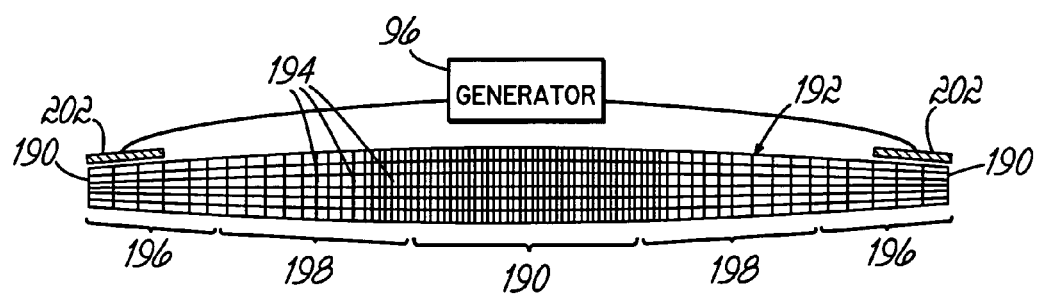

This critical distinction between the present embodiment and prior art applications is further accentuated in FIG. 11C, where subsequent, third pulses of applied resonant sequences continue to sustain sarcomere 184 bridges near the poles 180 as second pulses propagate to the intermediate portions. FIG. 11C shows such a scenario as both second and third pulses maintain tension within their respective muscle portions 188, 186. In this manner, tension is simultaneously maintained throughout the extreme and intermediate portions 186, 188 of the muscle 182 as the first pulses continue to propagate towards the center 190 of the muscle 182. Sarcomeres of the center 190 bridge to facilitate a uniform contraction across the entirety of the muscle 180. Of note, such uniformity evades the prior art application of FIG. 12C in that only the center portion 200 of the muscle 190 toggles while the intermediate 198 and extreme 196 portions relax.

In contrast, FIG. 11C shows the sarcomeres of the center portion 190 creating strong bridges in response to the first pulses of the resonant sequences. Significantly, all portions 186, 188 and 190 of the muscle 182, or musculature may be uniformly and simultaneously toggled. This feature is enabled by the optimized spacing and pulse variation of the resonant sequences, which are configured to mitigate nutritional and electrical exhaustion that frustrate prior art attempts to comparable contractile reactions. Such uniform stimulation can translate into more natural and deeper (resonant) contractions. Furthermore, the uniformity obviates much of the pain conventionally associated with sarcomere stretching. As discussed below in detail, variation of the pulse characteristics facilitates sustained sarcomere bridges enabling the uniformity shown in FIG. 11C by accounting for accommodation. Of note, additional pulses may be applied via the electrodes to further enhance uniformity as the contractile reaction propagates inwardly throughout the muscle 182 or musculature.

As such, a user may select a number of pulses at block 11 of FIG. 1 that will comprise a resonant sequence. As shown in the exemplary user interface 11 of FIG. 3, an operator may manipulate a dial 112 to specify how many pulses the generator 14 of FIG. 1 will include within an exemplary sequence having around a 7.6 millisecond span. Of note, a preferable setting for most healthy patients may comprise between four and seven pulses. The stimulator 12 of FIG. 1 may set the voltage of each selected pulse to account for pulse number and duration. Alternatively, the user may manually adjust voltage using dial 114 of the interface 11 of FIG. 3 to a setting preferably ranging from about 1 to about 150 volts. Of note, such range is merely exemplary and may be increased substantially in special cases, such as with a denervated patient.

In this manner, the interface 11 allows a user to optimize the number of pulses comprising a sequence such that sarcomere bridges of the musculature are maintained at the extremities of the musculature as subsequent pulses propagate toward its center. That is, while the resonant sequence is configured to induce only one, uniform contraction, the musculature may nonetheless register individual polarities and other parameters of the pulses of the sequence. As such, the individual charges of each pulse may evenly accumulate an aggregate charge across all tissues of the musculature. In this manner, the reinforced and evenly distributed bridges of the sarcomere provide a series of twitches sufficient to drive the contractile reaction. The absence of a large spiking voltages and muscle stretching associated with uneven muscle contraction achieves a more thorough contraction without the pain often associated with such conventional pulse trains.

The user may further optimize the number of pulses selected at the interface 11 of FIG. 3 to uniformly address different muscle types as the signal propagates throughout the body of the user. For instance, a resonant sequence containing four to seven pulses may incorporate a sufficient number of pulses to progressively stimulate the length of a musculature without overstimulating fast twitch tissue. As such, an operator may accordingly adjust a dial 112 and corresponding number of pulses in a sequence. Additionally, the pulses spacing between the selected number of pulses promotes a deep contraction in slow twitch tissues affected by the same signal. In this manner, the embodiment uniformly accommodates the different sensitivities of muscle groups.

Thus, a patient and/or technician may configure all of the pulse/sequence characteristics discussed herein via the exemplary user interface 11 of FIGS. 1 and 3. For instance and as discussed below in detail, an operator may adjust another dial 117 to determine the frequency of pulses associated with a signal. Most treatment applications preferably require anywhere from about 25 pulses per second to about 70 pulses per second. Another dial 113 may proportionally control the intensity or voltage associated with a signal relative to a second, simultaneously and proximately applied signal. As also discussed below, an operator may adjust the polarity and rest periods in between resonant sequences via dials 116 and 115, respectively.

Features of the interface 11 configured to receive input may comprise a series of dials as shown in FIG. 3. In the alternative, a combination of switches, keyboard, touch screen/pad, buttons, modem, microphone, or any other known input mechanism may be employed. Alternatively or in addition, a suitable user interface 11 may place little or no physical demands on a user. For instance, an exemplary interface 11 of FIG. 1 may include voice recognition software, or incorporate handles or pedals that may be manipulated by merely bumping or squeezing.

Figure 4:
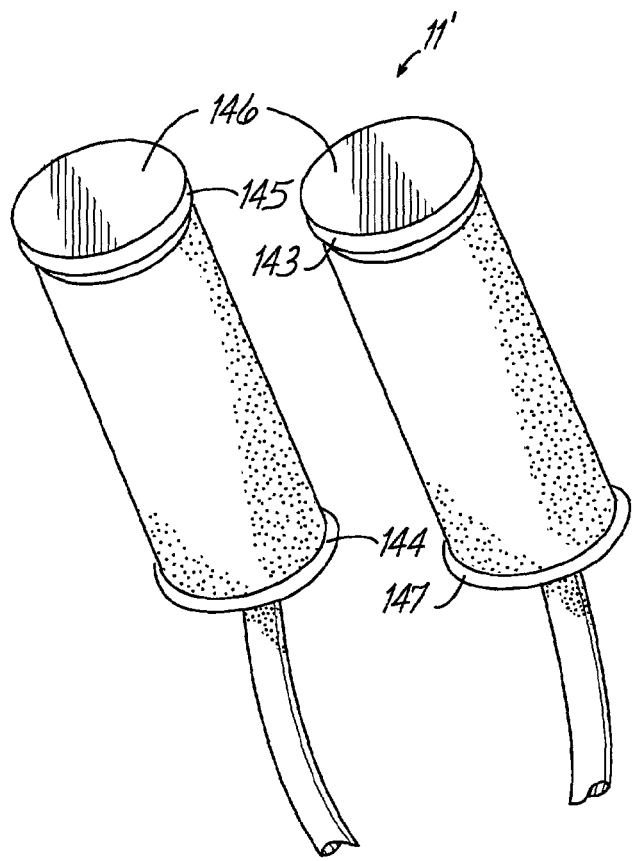
FIG. 4 shows a second user interface suited for implementation within the apparatus of FIG. 1.

For instance, exemplary handles 118 comprising the interface 11" of FIG. 4 may be manipulated by a user to control stimulator functions. As such, the user may grip orient, or contact the handles in such a manner as to affect the voltage, frequency and rest periods associated with resonant sequences. For instance, a user may reverse the polarity of resonant sequences by tapping opposite ends 143 and 144 of the handles 146 together. Such action may reduce stinging of the skin that may be associated with applications of uniform polarity. Another embodiment may interpret the same action as a request from the user to incrementally increase voltage. Conversely, tapping opposite ends 145 and 147 may cause a decrease in voltage. Contacting all four ends 143, 144, 145, 147 of the handles 146 may initiate a period of rest for the user, temporarily halting transmission of the stimulating signal. Other parameters, such as package rate and channel balance may be accessible to the user by contacting respective bottoms 144, 147 of the handles 146 together. Such contact may alternatively or in addition, change a mode of the application, altering command/contact sequences of the handles 146 to allow for the adjustment of additional parameters.

Figure 5:
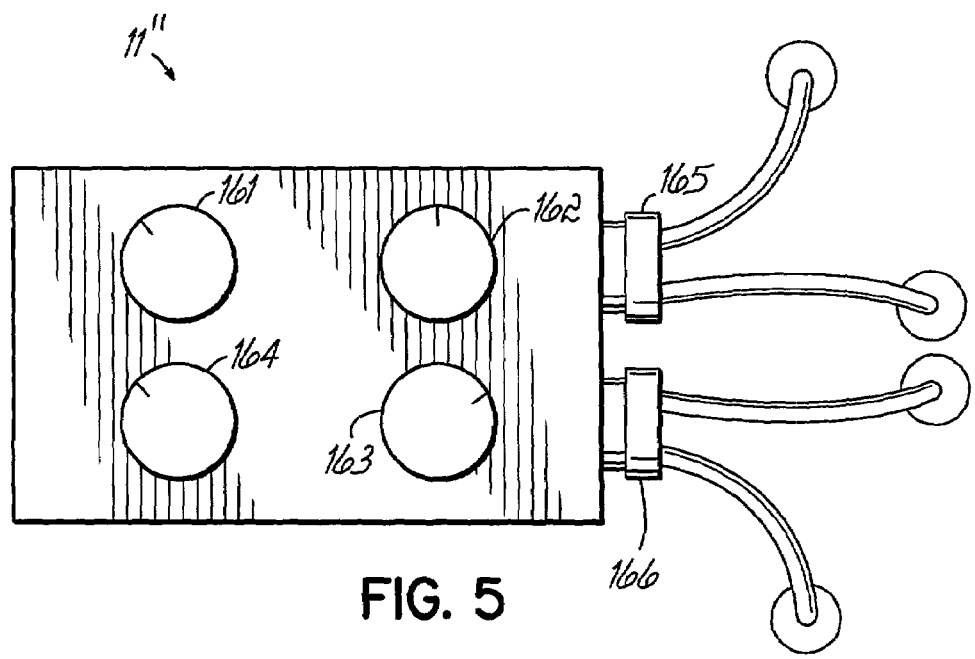
FIG. 5 shows a third user interface suited for implementation within the apparatus of FIG. 1 and configured to attach to clothing of a user.

Another embodiment illustrated in FIG. 5, shows a battery operated user interface 11" configured to fit within a pocket or otherwise attach to the clothing of a user. As with the larger, stationary embodiment shown in FIG. 3, the user interface 11" of FIG. 5 incorporates multiple dials 161–164 with which the wearer may adjust stimulator settings. More particularly, dial 161 may communicate required voltage levels to the stimulator, preferably ranging from a fraction of 1 volt to about 150 volts. Dial 162 may adjust, or balance, the relative voltage as applied between respective channels leaving ports 165, 166 of the interface 11".

In this manner, the interface 11" facilitates stimulating different muscle groups according to tailored voltage levels. Dial 163 may control the frequency of pulses generated by the stimulator, and dial 164 may interject a proscribed ratio of rest periods between resonant sequences. Of note, dials 161–164 are merely exemplary and could each be substituted or augmented with any number of functions controlling features of a stimulating signal, to include phasic modulation and/or waveform shapes. Also, the self-contained and portable nature of the user interface 11" enables a wearer to receive treatment while traveling, working or exercising.

A user interface of another embodiment may incorporate a hysteresis loop configured to monitor contractile, diagnostic or other patient/user reactions and automatically adjust signal generation, accordingly. For instance, the a sensor monitoring the heart rate of a patient may cause the stimulator 12 of FIG. 1 to step down voltage or interject a rest period in response to detecting an elevated rate. Morever, a suitable user interface may enable both the user and the operator to access the interface. As such, the feature allows an athlete or patient to adjust signal charge and other parameters of the stimulator signal per their own tolerance levels and unique fitness goals.

Of note, the inclusion and optimization of pulses at the user interface 11 of FIG. 1 further mitigates the effects of nutritional depletion and accommodation. In addition to initiating and sustaining sarcomere bridges throughout the musculature, the optimized spacing between each pulse further allows the musculature to perceive other characteristics of each pulse. As discussed below in detail, an operator may access the interface 11 to vary such pulse characteristics as polarity, amplitude, width and/or spacing as between pulses to realize additional benefits. For instance, such variation may limit the detrimental effects of accommodation on the sarcomere level. Ideally, the body will not have time to adjust between different characteristics, and a deep level of penetration may be maintained. Rest periods in between pulses may allow the musculature time to recalcify and replenish ATP, as well as electrically reset.

Another benefit realized by the pulse configuration feature of the interface 11 of FIG. 1 concerns patient discomfort. As discussed below, the variation of polarity as between respective pulses and sequences may be made to equalize each other where desirable, decreasing the occurrence of stinging surface sensation. Additionally, since the charge of each pulse of a given resonant sequence is relatively low, the applied signal does not subject the musculature to a single, large charge pulse of a type conventionally associated with pain. In this manner, the resonant sequence achieves a cumulative, high voltage charge without the detrimental side effects associated with a conventional single pulse.

In response to the user selecting the number of pulses comprising a resonant sequence, the stimulator 12 of FIG. 1 may automatically manipulate the polarity of respective pulses within a resonant sequence. For instance, the controller 16 may retrieve from memory 18 a polar profile, or template, that corresponds to the designated number of pulses. As such, the polar profile associates a preprogrammed polarity with each pulse of the resonant sequence. Within a given polar profile, a portion of the pulses may have a negative polarity, while the remainder exhibit positive characteristics.

The exemplary signal of FIG. 2 demonstrates such variation within each resonant sequence. For instance, the polarity of first 22 and fourth 24 pulses of a first resonant sequence are intermixed with pulses 26–28 of opposing polarity. Variation in polarity serves to break up accommodation in that change hinders the ability of the body to adjust to the pulses. Thus, the stimulator 12 of FIG. 1 adjusts polarity in response to input from the user interface 11 to enable greater penetration for subsequent pulses of a resonant sequence.

As shown in the interface 11 of FIG. 3, the user may further be prompted to alter the polarity of an entire resonant sequence. For instance, a user may turn a dial 116 on the interface 11 to select a number of consecutive resonant sequences to be generated before a sequence having opposite polarity is presented. The exemplary signal of FIG. 2 has two resonant sequences 30, 32 that are polar opposites of each other. In this manner, the settings of the interface 11 of FIG. 3 provide at least two layers of phasic variation (at both the pulse and resonant frequency levels) to promote deep muscle contraction and limit surface stinging.

The controller 16 of FIG. 1 additionally executes program code 17 configured to manipulate the cumulative polarity of the resonant sequences of a signal. That is, a program 17 may mathematically manipulate the order and number of resonant sequences within a signal to achieve a desired balanced or net charge. For instance, the controller 16 may repeat, insert and delete resonant sequences to ensure a desired proportion of total signal charge is oriented at a specific polarity. As such, the controller may minimize surface charge and associated stinging by achieving a balanced charge.

Alternatively, the program 17 of FIG. 1 may configure resonant sequences so as to induce a uniform flow of electrical charge. Such a net charge may be appropriate where the operator wishes to open or constrict targeted blood vessels. Similarly, the program may employ a net charge to squeeze or otherwise influence the function of lymph nodes or veins. As such, a suitable user interface 11 of FIG. 1 may include four settings. One such setting of the interface 1 may include a first control for normal charge distribution. A second, exemplary setting may correspond to a moderately unbalanced, net charge. More extreme applications, such as may be appropriate for some denervated patients, call for gross unbalancing, or even uniform polarity.

Figure 6:
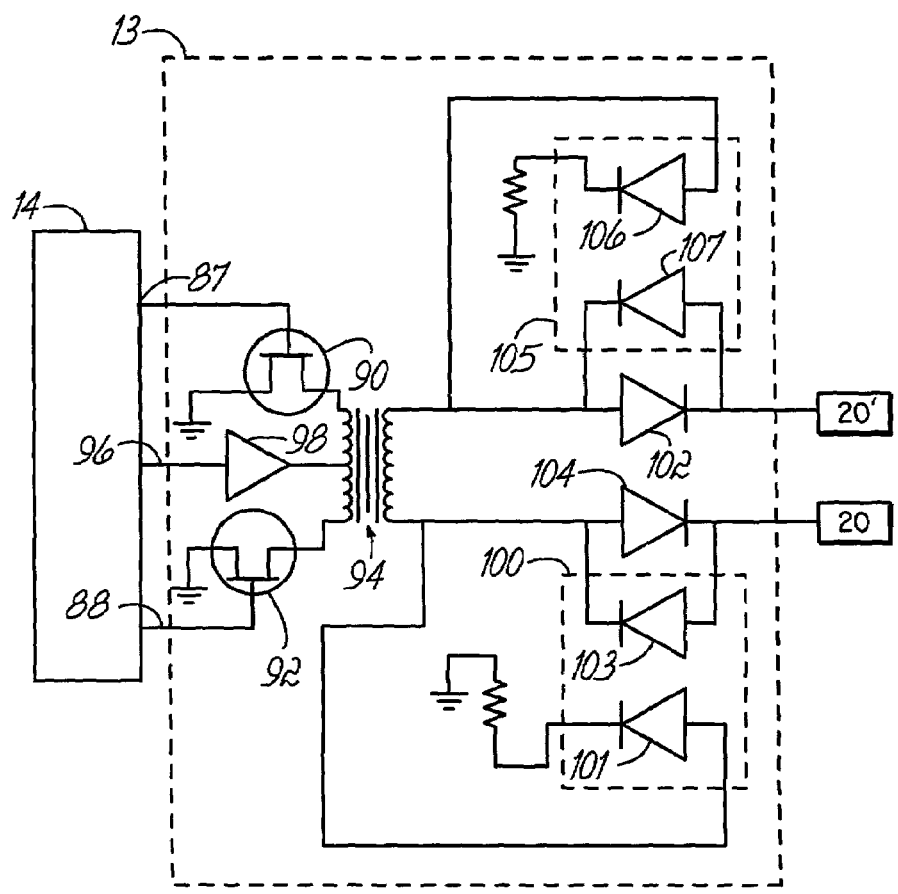
FIG. 6 illustrates in greater detail the output and polarizing circuitry block in the apparatus of FIG. 1.

FIG. 6 shows an exemplary circuit suitable for implementing polarizing circuitry 13 of FIG. 1 in such a manner as to prevent a pulse from overshooting zero voltage upon its termination. An inability to regulate polarity as such otherwise results in a net electrical imprecision. As shown in FIG. 6, such polarity may be facilitated by polarizing circuitry 13 comprising switching transistors 90, 92 and optical diodes 102, 104 configured to regulate current flow in one direction.

More particularly, a signal transmitted from the generator 14 arrives at the polarizing circuitry 13 via lines 87. As discussed below, the signal conveys its own series of resonant sequences tailored according to user input. For efficiency and hardware consideration, the voltage associated with the signal remains relatively low when leaving the stimulator. Consequently, the voltage associated with the signal must be increased prior to transcutaneous application at an electrode 20. To this end, the signal passes through a switching transistor 90 to a transformer 94.

The transformer 94 steps up the voltage of the signal according to a voltage command transmitted from the generator 14 via line 96 and amplifier 98. The voltage command operates to apply voltage to the transformer 94 and thus affect how much the voltage of the signal is stepped up. The voltage signal from the generator 14 may correlate to user input, for instance, dialed-in to the intensity setting 114 of FIG. 3. This feature enables the magnitude of pulses to be varied according to therapeutic protocol and user tolerance. For instance, a user may vary voltage of a pulse between about 1 and about 150 volts.

The switching transistor 90 may continue to relay the signal to the transformer 94 so long as voltage presented at its gate remains above a threshold voltage associated with the transistor 90. Should the voltage presented by the signal at the gate fail to achieve the threshold level, then the transistor 90 will become unsaturated and the voltage signal will drain to ground. Subsequently, no signal will be presented to the transformer 94 for that period where voltage remains below the threshold level. Of note, the threshold level and signal voltage may be coordinated such that signal will present a voltage at least equaling the threshold level at a point of a resonant sequence corresponding to a pulse. Thus, the binary nature of the switching transistor 90 configuration may ensure that only voltage associated with pulses is passed to an electrode 20.

In this manner, the transformer 94 steps up the voltage associated with the pulse signal 87 prior to shaping it with an opto-isolator 100 and rectifying diodes 104. Absent such provision, transformer output would oscillate and swing above zero voltage at the terminal ends of each pulse. Such imprecision could negatively affect aggregate charge related to a user via the electrode 20. Consequently, the opto-isolator 100 receives the stepped up signal and acts as another layer of polar filtration.

More particularly, an LED 103 of the opto-isolator 100 emits light in response to detecting current conveyed by the signal. A light sensing device 101 of the opto-isolator 100 detects the illumination and sends a signal to a rectifying diode 104, which further ensures the uniform and intended polarity of the signal. Thus, these components act in tandem to clip transformer output at the terminal end of a presented pulse. While the inclusion of the opto-isolator 100 obviates a requirement for an electrical connection and associated ground loops, it should be understood by one of ordinary skill that their functionality could be replaced by switches and relays. Of note, the circuitry 13 of FIG. 6 makes allowance for two different signals, transmitted over lines 87 and 88. As such, the exemplary circuitry 13 provides a second opto-isolator 105 configurable to communicate current and flow to a second rectifying diode 102 prior to transcutaneous application to the user via electrode 20'.

Likewise, the apparatus 10 of FIG. 1 enables the simulator 12 to simultaneously apply different resonant sequences to a muscle and/or muscle group. For instance, the generator 14 may retransmit the original signal to a second electrode 20. As discussed above, the electrodes preferably apply their associated signals near respective ends of the musculature. Alternatively, the stimulator 12 may initiate the transmission of some phasic variant of the original signal to the second electrode 20. The generator 14 may transmit the additional signals in such a manner as to realize interactive or synergistic effects between the signals discussed detail in below. As such, at least two signals may be proximately applied and synchronized such that the combined application emulates a single pulse having a width that exceeds the parameters of a conventional transformer.

This feature enables an operator to tailor pulse frequency towards holistic muscle development. For instance, one embodiment of the present invention has particular application when attaching electrodes 20 of FIG. 1 at extremities. The highest concentrations of fast twitch muscles are generally in the extremities to provide speed and fine control to the hands and feet. As discussed above, fast twitch muscles react quickly to individual pulses of a resonant sequence. The pulse spacing within a resonant sequence allows the fast twitch muscle to recover in between pulses in manner that avoids overstimulation and nutritional depletion. The optimized spacing of the pulses of an applied resonant sequence further enables the formation of sarcomere bridges within slow twitch fibers of the muscle. Thus, charges of the individual pulses affect twitches uniformly throughout the musculature.

The sustained bridges of the sarcomere are accommodated by variation in pulse characteristics that register within the musculature. More particularly, variation in pulse polarity, width, amplitude and spacing can combat accommodation and enable greater penetration with less discomfort. As such, a signal applied to the hand of a user may seem comfortable to the fast twitch muscles of the carpal tunnel and forearms, while simultaneously stimulating the upper muscles of the upper arm and chest. Similar applications may be realized with the respective fast and slow twitch muscles of the feet and legs of a user. In this manner, the apparatus 10 capitalizes on the natural timing of muscle processes.

Of note, while the invention has and hereinafter will be described in the context of a stimulator, controller, computer or other processor, those skilled in the art will appreciate that the various embodiments of the invention are capable of being distributed as a program product in a variety of forms, and that the invention applies equally regardless of the particular type of signal bearing medium used to actually carry out the distribution. Examples of signal bearing media include but are not limited to recordable type media such as volatile and non-volatile memory devices, floppy and other removable disks, hard disk drives, magnetic tape, optical disks (e.g., CD-ROM's, DVD's, etc.), among others, and transmission type media such as digital and analog communication links.

Morever, various programs described herein may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Figure 7:
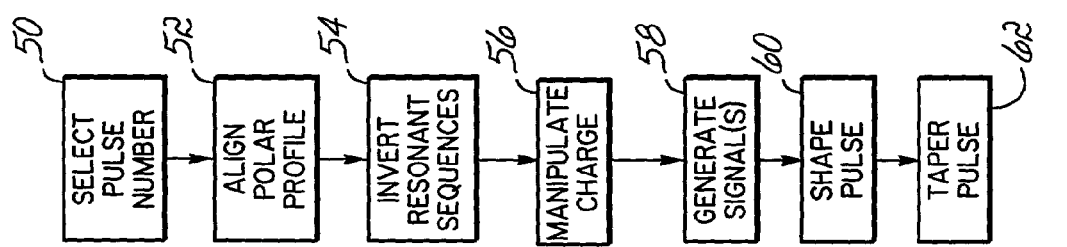
FIG. 7 illustrates a series of steps suited for execution within the apparatus of FIG. 1.

The flowchart of FIG. 7 illustrates sequence steps suited for execution within the system hardware environment of FIG. 1. Namely, the exemplary steps are suited to generate a resonant sequence in accordance with the principles of the present invention. As discussed above, each resonant sequence preferably contains at least three pulses. Regarding FIG. 3, the stimulator may select the number of pulses included within a sequence at block 50 in response to user input.

As such, each resonant sequence will include periods of rest in between pulses. After each pulse of a resonant sequence, a musculature may require a period of time to replenish some of the ionized calcium and ATP's lost in reacting to the preceding pulse of the resonant sequence. This replenishment enhances the strength of the next twitch and breaks up accommodation in the sarcomere and fibril levels. The number of pulses comprising a sequence can further be optimized to propagate a contractile reaction across a musculature while sustaining tension throughout. The number of pulses may additionally influence the extent to which the musculature is stimulated by the generated signal. This consequence is a product of how different muscle groups react to stimuli.

For instance, a fast twitch muscle of a musculature may react to every pulse within a resonant sequence. As such, the number of pulses in a sequence may be set at block 50 according to a number or frequency that does not result in excessive downtime in between pulses. Such precaution helps avoid painful jerking reactions and under stimulation in fast twitch muscles. Because a slow twitch muscle can not respond as quickly to the potentials of high frequency pulses, care is taken to configure pulses so as to compliment the natural, harmonic frequency of the slow twitch muscle.

For instance, while a resonant sequence containing over eight pulses may be too fast to register with the slow muscle, a smaller, optimized number of pulses within a sequence may achieve a resonant affect. That is, the charge of the pulses initiates and sustains bridging of sarcomeres throughout the musculature leading to a single, synergistic pulse. Of note, care is taken not to overload the fast twitch muscles. As such, the fast twitch muscles have time to recover in between pulses, translating into decreased tension and pain. As with many of the settings addressed herein, the number of pulses in a resonant sequence required to achieve a maximum harmonic affect may vary according to the condition and tolerance of the user. For instance, a patient with severe muscle denervation may tolerate over seven pulses within a resonant sequence. In many cases, however, the four to seven pulses per burst demonstrates optimum results.

Having used the interface to specify the number of pulses at block 50, program code executed by the controller may assign a polar profile to the resonant sequence at block 52. Namely, the controller may associate the requested number of pulses with a polar profile or template maintained within the database. As such, the polar profile associates the requested number of pulses with predetermined polarities. The database may store multiple combinations of such polar profiles for each pulse count. As discussed above, polarity may vary to combat accommodation, as well as to adjust net charge. Alternating polarity can facilitate maintaining tension across the musculature, as the feature can mitigate the affects of accommodation that could break sarcomere bridges or necessitate more voltage.

Having varied the polar sequences of pulses within a single resonant sequence at block 52, the stimulator may alter the polarity of each resonant sequence at block 54. More particularly, an operator may specify the number of resonant sequences generated before the polarity of a resonant sequence or group of resonant sequences is inverted. For instance, a user interface may prompt an operator to specify that the polarity of resonant sequences should be reversed after every three sequences. As above, changes in polarity can mitigate the effects of accommodation. Absent such variation, a musculature may begin to adapt to a repeated pulse pattern after a few cycles, compromising penetration. By reversing the polarity of the resonant sequence, a musculature may perceive the inverted resonant sequence as being an entirely distinct resonant sequence. As such, a musculature that has adjusted itself to accommodate a given resonant sequence may nonetheless react to the same sequence with reverse phasing. In this manner, the stimulator provides layers of phasic variance at both the pulse and resonant sequence levels.

At block 56 of FIG. 7, the stimulator may vary the order of inverted resonant sequences to obtain mathematical consistency with regard to phasing and pulse length. The goal of the manipulation may include realizing a balanced or desired net charge. For instance, the controller may mathematically manipulate resonant sequences to ensure a desired proportion of signal charge is oriented at a specific polarity. In most cases, the controller will repeat, insert and delete resonant sequences to realize a balanced charge, minimizing surface charge and associated stinging.

In another application at block 56, an operator may desire to induce a uniform flow of electrical charge. Such a net charge may be appropriate where the operator wishes to open or constrict targeted blood vessels. Similarly, the stimulator may employ a net charge to manipulate the function of lymph nodes and the contractions of localized cells. As such, an exemplary user interface may include four settings. For instance, suitable settings of an interface may include one for normal distribution and a second setting configured to promote minor unbalance. More extreme applications may call for a grossly unbalanced charge, or even uniform polarity.

The stimulator may then generate a first signal at block 58 in accordance with the specified resonant sequence parameters. As such, the signal may be transmitted via the electrode to the musculature. Preferred applications may call for the generation of additional signals at block 58. The stimulator may employ the additional signals in such a manner that a synergistic or compound effect is realized. For instance, the coordinated charge of two proximately applied signals can emulate a single, longer pulse. Of note, the pulse width and voltage realized by such a configuration may exceed that available via a single generating transformer. As such, the dual signal feature can overcome equipment limitations to achieve greater muscle penetration. As discussed below, additional compounding and harmonic effects may be achieved by simultaneously applying multiple signals.

To this end, the controller may reuse the profile used to recreate the original signal at block 58. As such, the generator may transmit the original signal to a second electrode at block 58. Alternatively, the generator may initiate the transmission of some phasic variant of the original signal to the second electrode. An exemplary user interface configured to account for such phasic variation may include a dial, touch pad or other mechanism configured to select from among different signal generation schemes.

Figure 8:
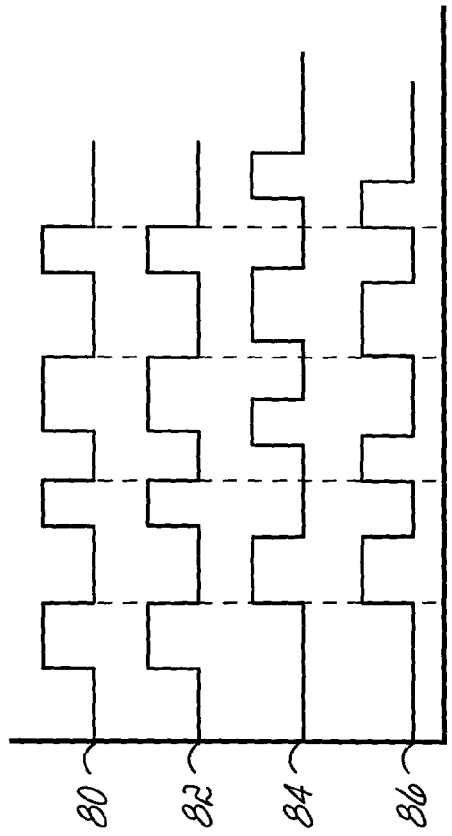
FIG. 8 illustrates four exemplary signals that may be generated and simultaneously applied within the apparatus of FIG. 1.

FIG. 8 illustrates three exemplary signals that may be applied to the user in conjunction with an original signal 80. More particularly, the exemplary in-phase application 82 of FIG. 8 may be applied to a user via a second electrode placed proximate to the first, which conveys the original signal 80. As such, the in-phase signal 82 mirrors the resonant sequences of the original channel 80. In this manner, signal strength is reinforced as both channels propagate throughout the user. A third channel 84 may duplicate the original signal 80 beginning at the end of the first pulse 85 of the original 80. Still a fourth application may cause each pulse of the resultant signal 86 to initiate at the end of each pulse of the original signal 80. A musculature may perceive such an application as having seamless pulses of twice the width of the original pulse 80. Such a design can have particular application where denervated patients require pulses of greater width than are available via conventional transformers.

All three signals illustrated in FIG. 8 are appropriate for therapeutic application, two signals 84, 86 further facilitate muscle growth. Of note, the order in the which the channels are transmitted may vary relative to one another. For instance, one application may call for an original signal 80 transmitted via a first electrode to be followed by the out-of-phase signal 84 emanating from a second electrode. To achieve greater muscle penetration, the controller may reverse the relative order of the signals such that the original signal 80 executes in succession to the other 84. This feature represents yet another layer of variation available to overcome accommodation.

In this manner, the changing phasic relationship of two signals may combine to generate deeper muscle contractions with less associate discomfort. That is, the body will not have time to adjust to or brace for changes in the signal sequence. Consequently, applied charges need not be increased to maintain constant levels of stimulation. Because applied charge can be proportional to patient discomfort, the stimulator enables more contractile reaction with less pain. As discussed above, the exemplary user interface 11 of FIG. 3 may further allow a user to adjust the relative strength of two signals in proportion to each other.

As may be appreciated, the inclusion of additional signals can realize still further penetration and additional subharmonics. For instance, the stimulator may simultaneously employ three signals to different electrodes. The controller may further redirect respective signals to different electrodes and corresponding muscle groups. Such an application may promote balanced muscle development while breaking up accommodation.

Also of note, the flexible interface and electrode configuration of the above described embodiment may enable an athlete or patient to perform athletic or therapeutic motions while the stimulator concurrently exercises the musculature. As such, an operator may limit applied electrodes to a number sufficient to avoid encumbering the athlete from accomplishing a desired range of motion. For instance, a user may simulate an arm swing appropriate for a tennis racket, baseball bat or golf club while electrodes on the swinging arm communicate muscle building signals. This feature enables a musculature of the athlete to be stimulated at different stages of contraction, translating into more balanced muscle development and training.

Figure 9:
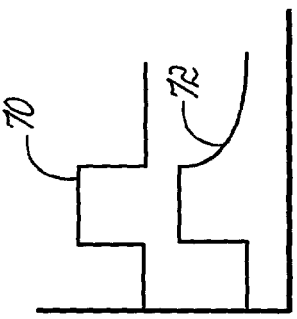
FIG. 9 shows exemplary pulse shapes generated by the apparatus of FIG. 1 and suited for incorporation into the signal of FIG. 2.

Returning to FIG. 6, the stimulator may manipulate the shape of each pulse at block 60 to capitalize on the manner in which nerves of the body react to stimuli. For instance, FIG. 9 shows a conventional square pulse 70 that the may be generated in accordance with the principles of the invention. Such a square pulse 70 may have particular application where a user requires relatively more rest in between pulses to replenish lost resources. FIG. 9 additionally illustrates another pulse formation 72 available for generation within the confines of the present embodiment. As shown in the figure, the trailing edge of the pulse 72 exemplifies faradic characteristics. That is, the trailing edge of the pulse lingers and trails off.

This trailing, or faradic feature shown in FIG. 9 causes the pulse 72 to more gradually discharge throughout the musculature in a manner analogous to that of a capacitor in a circuit. In fact, one embodiment may cause a transistor to discharge an actual capacitor into the skin of the user in response an absence of current in order to form the pulse 72. A resistance circuit may further contribute to the natural resistance of the skin to facilitate voltage bleed off. Alternatively, a generator or transistor may be tasked to form a faradic wave at low voltage. Such a waveform may be amplified at output.

A sensory nerve processing a pulse 72 of FIG. 9 produced in such a manner may perceive the immediate portion of the trailing edge as constituting the end of the signal. This feature may serve to relax and calm the sensory nerve, diminishing the occurrence of muscle tightening. Significantly, a motor nerve reacting to the same pulse 72 may continue to react to the trailing portion of the pulse 72. In this manner, the embodiment extends the period of work affecting the musculature without unduly taxing sensory nerves.

Significantly, the decaying pulse 72 of FIG. 5 is more like what the body naturally produces than the conventional square pulse 70. Such characteristics are desirable because nerve fibers make for relatively poor conductors absent the natural, active processes of the muscle. Consequently, emulation of natural impulses realized by the pulse sculpting feature of block 60 of FIG. 7 invokes natural processes and promotes current flow at lower voltages. As such, applied charges may alternatively be increased to achieve deeper contractions. Of note, both types of pulses shown in FIG. 9 can be used in tandem to vary stimuli and overcome accommodation.

Figure 10:
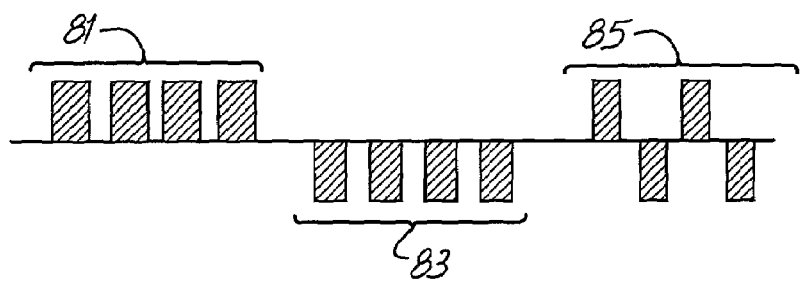
FIG. 10 shows resonant sequences that taper in accordance with the principles of the present invention.

In nature, signals from the brain taper to allow replenishment and enhance the strength of a next occurring twitch. Acknowledging this phenomenon, the stimulator at block 62 of FIG. 7 may shorten the width of successive pulses of a resonant sequence as a muscle tires. For instance, the duration of pulses included in resonant sequences 81, 83, 85 of FIG. 10 gradually taper on the order of ten to twenty percent. The width of successive pulses of resonant sequence 30 of FIG. 2 similarly wane. In this manner, a musculature perceives the decaying signal as being more like those naturally produced by the body.

The shortened pulse width will also decrease pain at the fascicle tissue level. Of note, this feature enables contractile responses at lower charge levels. Consequently, the stimulator may operate at charge levels that induce less pain in a user. As such, the feature allows a user to comfortably increase charge to allow greater penetration and overcome accommodation. Similarly, width may vary as between consecutive resonant sequences to achieve other comfort and therapeutic benefits. Furthermore, one skilled in the art should recognize that the order of pulses of varying width, shape or magnitude need not require one pules to immediately follow another, any sequence of like and dissimilar pulses may be generated in accordance with the principles of the present invention.

Despite the rest periods and other provisions built-in to the generated signal, certain users may require additional rest to more thoroughly replenish lost ATP and ionized calcium. Consequently, one embodiment may include a rest-on-demand function. As such, a user may manipulate the interface 11 of FIG. 1 to pause the transmission of signals to the electrode(s). For example and as discussed above in the text accompanying FIGS. 3–5, a user may bump a handle 118 or petal configured to temporarily cease transmission in response to contact.

Of note, because generated signals of the embodiment balance electrical polarities and replenish lost resources continuously, the musculature may require only a few seconds of rest to completely recover. Furthermore, such short rest periods may be preprogrammed into a treatment or training protocol. Of note, one embodiment slowly ramps up the voltage following a such downtime to facilitate a gradual, relatively painless transition.

It will be appreciated that the generation of the various resonant sequence profiles and associated pulse shapes discussed herein may be implemented using hardware and/or software to store and/or generate the appropriate profiles and shapes, and that such implementations would be within the abilities of one of ordinary skill in the art having the benefit of this disclosure.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of stimulating a musculature including slow twitch muscle fibers, the musculature positioned between first and second electrodes disposed at opposite ends of the musculature, comprising:

applying a resonant sequence of pulses across the musculature via a plurality of electrodes, wherein the resonant sequence includes at least three pulses, and wherein the pulses of the resonant sequence are spaced at around 3,500–7,000 microseconds relative to one another such that each pulse subsequent to a first pulse in the sequence is effective to progressively stimulate and create tension in the musculature inwardly from the electrodes and towards the center of the musculature to uniformly initiate a contraction within the musculature while maintaining the tension created in at least a portion of the musculature by each preceding pulse in the resonant sequence.

2. The method according to claim 1, wherein generating the resonant sequence includes generating the resonant sequence to have first and second pulses that have a different pulse characteristic.

3. The method according to claim 2, wherein the different pulse characteristic is selected from among a group comprising: width, amplitude, spacing, polarity, shape and some combination thereof.

4. The method according to claim 2, wherein the first and second pulses have polarities determined according to a polar profile.

5. The method according to claim 1, wherein generating the resonant sequence includes generating the resonant sequence to have first and second pulses that have an identical pulse characteristic.

6. The method according to claim 5, wherein the identical pulse characteristic is selected from among a group comprising: width, amplitude, spacing, polarity, shape and some combination thereof.

7. The method according to claim 1, further comprising generating a second resonant sequence.

8. The method according to claim 7, wherein the first resonant sequence has a different parameter from that of the second resonant sequence.

9. The method according to claim 8, wherein the different parameter is selected from among the group comprising: width, amplitude, spacing, polarity, shape and some combination thereof.

10. The method according to claim 7, wherein the first resonant sequence and the second resonant sequence are in phase.

11. The method according to claim 7, wherein the first resonant sequence and the second resonant sequence are out of phase.

12. The method according to claim 7, wherein the first resonant sequence has an identical parameter to that of the second resonant sequence.

13. The method according to claim 12, wherein the identical parameter is selected from among the group comprising: width, amplitude, spacing, polarity, shape and some combination thereof.

14. The method according to claim 1, wherein generating the resonant sequence includes generating the pulses in the resonant sequence according to a selected number of pulses.

15. The method according to claim 1, wherein generating the resonant sequence includes generating the polarity of pulses so as to achieve a net charge.

16. The method according to claim 1, wherein generating the resonant sequence includes generating the polarity of pulses so as to achieve a balanced charge.

17. The method according to claim 1, wherein generating the resonant sequence includes generating at least one pulse of the plurality of pulses to have a trailing, faradic waveform characteristic.

18. The method according to claim 1, wherein at least one pulse of the plurality of pulses is a square waveform.

19. The method according to claim 1, wherein generating the resonant sequence includes generating a successive pulse of the plurality of pulses with a shorter width than a preceding pulse of the plurality of pulses.

20. The method according to claim 1, wherein generating the resonant sequence includes generating a first resonant sequence to have a shorter width than a second resonant sequence.

21. The method according to claim 1, wherein generating the resonant sequence includes generating the resonant sequence in response to input from a user interface.

22. The method according to claim 21, wherein the input received from the user interface concerns a parameter selected from a group consisting of: voltage intensity, pulse rate, pulse duration, charge balance, phasic modulation, rest periods and some combination, thereof.

23. The method according to claim 21, further comprising configuring the user interface to attach to a wearer.

24. The method according to claim 23, wherein the user interface a fits within a pocket of the wearer.

25. The method according to claim 21, wherein the user interface transmits the input in response to commands received from a source selected from a group consisting of: a handle, pedal, dial, button, switch, voice recognition software, diagnostic equipment, motion sensor and some combination, thereof.

26. The method according to claim 1, further comprising applying at least one additional resonant sequence to a user.

27. An apparatus for stimulating a muscle that contracts in response to a threshold potential, comprising:
a stimulator configured to produce at least one signal for transcutaneous delivery to a musculature that includes slow twitch muscle fibers, the musculature positioned between at least two electrodes, the stimulator being operable to apply a resonant sequence of pulses across the electrodes, wherein the resonant sequence includes at least three pulses, and wherein the pulses in the resonant sequence are spaced at around 3,500–7,000 microseconds relative to one another such that each pulse subsequent to a first pulse in the sequence is effective to progressively stimulate and create tension in the musculature inwardly from the electrodes and toward the center of the musculature to uniformly initiate a contraction within the musculature while maintaining the tension created in at least a portion of the musculature by each preceding pulse in the resonant sequence.

28. The apparatus according to claim 27, wherein the signal is transcutaneously delivered to the user via at least one electrode.

29. The apparatus according to claim 27, wherein a pulse characteristic differs as between a first and second pulse of the plurality of pulses.

30. The apparatus according to claim 29, wherein the stimulator configures the pulse characteristic to be identical as between the first and second pulse of the plurality of pulses.

31. The apparatus according to claim 29, wherein the pulse characteristic is selected from among a group comprising: width, amplitude, spacing, polarity, shape and some combination thereof.

32. The apparatus according to claim 27, wherein the stimulator configures a parameter of the first resonant sequence differently than that of a second resonant sequence.

33. The apparatus according to claim 32, wherein the stimulator configures the parameter of the first resonant sequence to be identical to that of the second resonant sequence.

34. The apparatus according to claim 32, wherein the parameter is selected from among the group comprising: width, amplitude, spacing, polarity, shape and some combination thereof.

35. The apparatus according to claim 32, wherein the first resonant sequence and the second resonant sequence are in phase.

36. The apparatus according to claim 32, wherein the first resonant sequence and the second resonant sequence are out of phase.

37. The apparatus according to claim 27, wherein the stimulator initiates retrieval of a polar profile having a group of pulses with preset polarities.

38. The apparatus according to claim 27, wherein the stimulator initiates selecting a number of pulses in the resonant sequence.

39. The apparatus according to claim 27, wherein the stimulator assigns polarities of a plurality of resonant sequences to achieve a net charge.

40. The apparatus according to claim 27, wherein the stimulator assigns polarities of a plurality of resonant sequences to achieve a balanced charge.

41. The apparatus according to claim 27, wherein at least one pulse of the plurality of pulses has a faradic characteristic.

42. The apparatus according to claim 27, wherein at least one pulse of the plurality of pulses is a square waveform.

43. The apparatus according to claim 27, wherein the stimulator initiates shortening a width of a successive pulse of the plurality of pulses.

44. The apparatus according to claim 27, wherein the apparatus is configured to attach to clothing of a user.

45. The apparatus according to claim 44, wherein the stimulator is configured to fit within a pocket of the user.

46. The apparatus according to claim 27, wherein the stimulator instructs the generator to generate at least one additional signal.

47. The apparatus according to claim 27, wherein the stimulator receives input from a user interface.

48. The apparatus according to claim 47, wherein the input received from the user interface concerns a parameter selected from a group consisting of: voltage intensity, pulse rate, pulse duration, charge balance, phasic modulation, rest periods and some combination, thereof.

49. The apparatus according to claim 47, wherein the user interface attaches to the user.

50. The apparatus according to claim 49, wherein the user interface a fits within a pocket of the user.

51. The apparatus according to claim 47, wherein the user interface transmits the input in response to commands received from a source selected from a group consisting of: a handle, pedal, dial, button, switch, voice recognition software, diagnostic equipment, motion senor and some combination, thereof.

52. A program product, comprising:
   a program for stimulating a musculature that includes slow twitch muscle fibers, the musculature being positioned between at least a first and second electrode respectively disposed at opposite ends of the musculature, the program configured to initiate an application to the musculature of a resonant sequence of pulses via the electrodes, wherein the resonant sequence includes at least three pulses, and wherein the pulses in the resonant sequence are spaced at around 3,500–7,000 microseconds relative to one another such that each pulse subsequent to a first pulse in the sequence is effective to progressively stimulate and create tension in the musculature inwardly from the electrodes and toward the center of the musculature to uniformly initiate a contraction within the musculature while maintaining the tension created in at least a portion of the musculature by each preceding pulse in the resonant sequence; and
   a signal bearing medium bearing the program.

53. The program product of claim 52, wherein the signal bearing medium includes at least one of a recordable medium and a transmission-type medium.

* * * * *